United States Patent [19]

Giacometti

[11] Patent Number: 4,921,501
[45] Date of Patent: May 1, 1990

[54] STEM FOR A PROSTHETIC FEMORAL HEAD

[75] Inventor: Roberto Giacometti, Milan, Italy

[73] Assignee: Sulzer Brothers Limited, Winterthur, Switzerland

[21] Appl. No.: 315,437

[22] Filed: Feb. 23, 1989

[30] Foreign Application Priority Data

Feb. 26, 1988 [CH] Switzerland ............................ 720/88

[51] Int. Cl.⁵ .............................................. A61F 2/32
[52] U.S. Cl. ......................................... 623/23; 623/18
[58] Field of Search ........................ 623/16, 18, 22, 23

[56] References Cited

U.S. PATENT DOCUMENTS 4,808,186 2/1989 Smith ..................................... 623/23

FOREIGN PATENT DOCUMENTS 0222236 5/1987 European Pat. Off. .............. 623/23
2627569 12/1977 Fed. Rep. of Germany ........ 623/23
2578738 9/1986 France ................................... 623/23

Primary Examiner—Ronald L. Frinks
Attorney, Agent, or Firm—Kenyon & Kenyon

[57] ABSTRACT

The stem is formed in the distal zone with a hollow and a longitudinal slot. The hollow is increasingly offset medially from the stem axis in the proximal direction while the slot is disposed in a plane defined by the longitudinal axis of the stem and neck axis. The stem has a resilience which increases distally within the distal zone to accommodate re-operation procedures while resisting lateral loadings imposed via the femoral head.

6 Claims, 2 Drawing Sheets

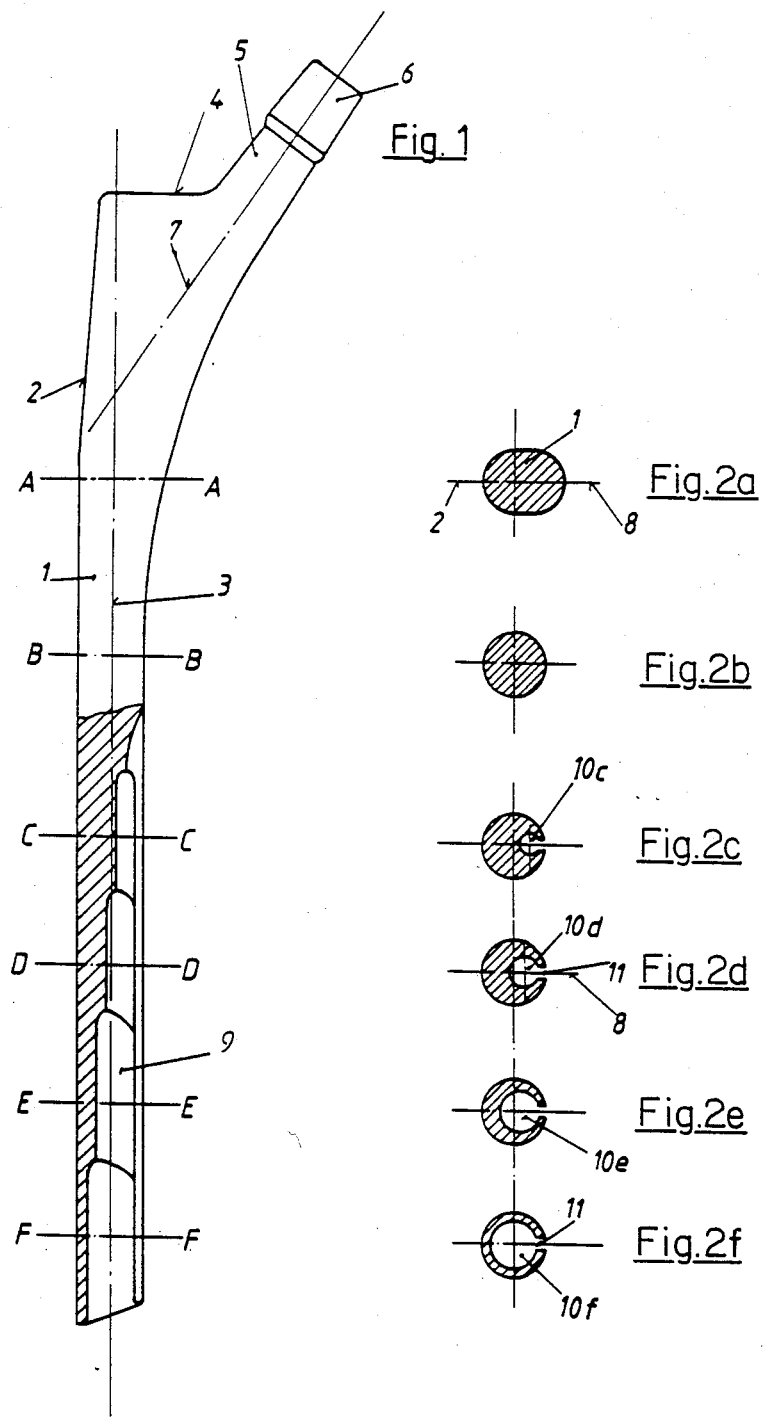

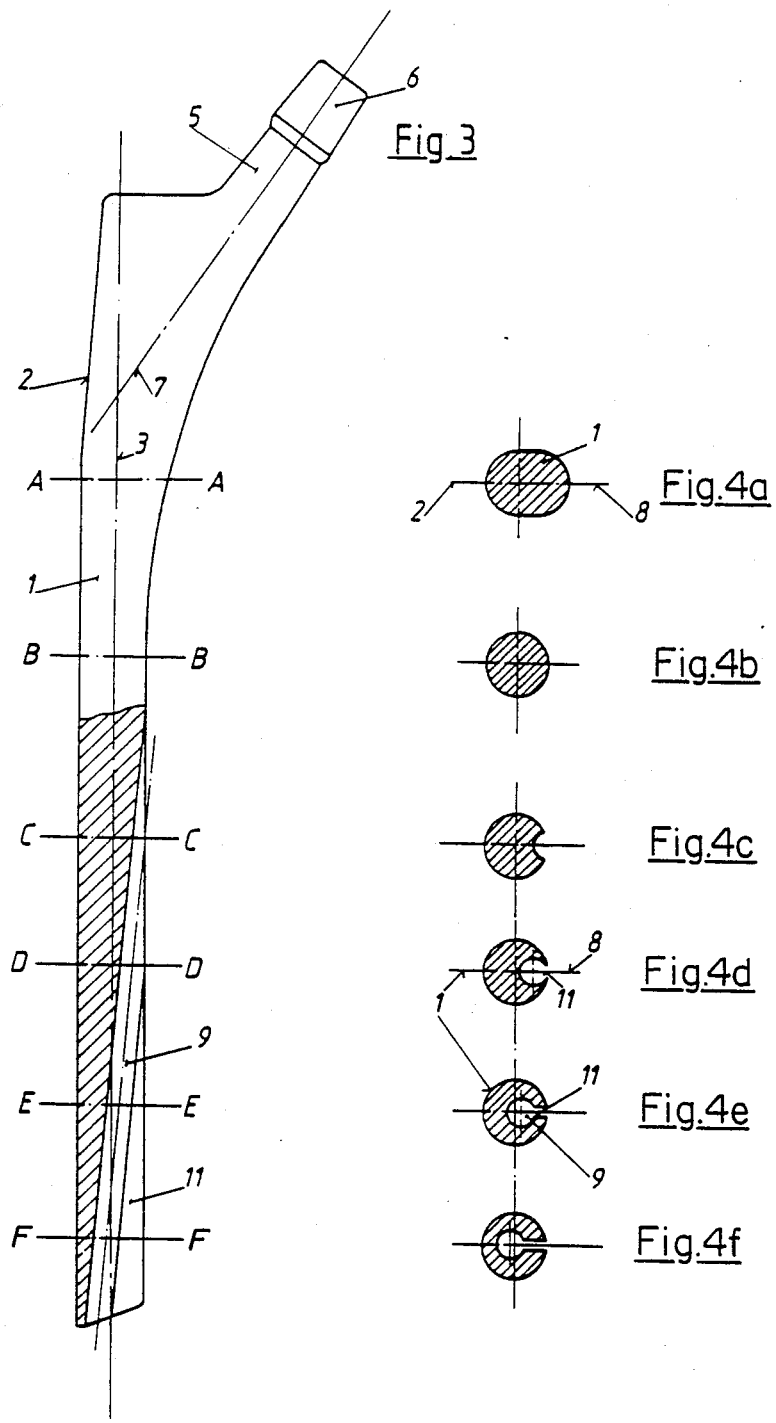

STEM FOR A PROSTHETIC FEMORAL HEAD

This invention relates to a stem for a prosthetic femoral head. More particularly, this invention relates to a shank for a hip joint prosthesis.

Heretofore, various types of constructions have been known to be used for the stem of a prosthetic femoral head in order to fix a hip joint prosthesis in a femur. For example, German OS2627569 and French Patent 2578738 describe various types of shaped shanks for the mounting of a hip joint prosthesis in a bone. In addition, European Patent Application 0222336 describes a fixing stem for a prosthetic femoral head wherein a distal end of the stem which is of round crosssection is formed with a central bore along the longitudinal axis of the stem as well as a pair of slots in the surrounding wall which are normal to each other in order to subdivide the wall into four discrete segments. The function of the bore and slots is to facilitate deformations, particularly, a compression of the distal end due to unevenness and a narrowing of an operation cavity in a femur.

As is known, because of the usual bending loads applied by way of a femoral head to the stem of a prosthesis, the distal zone of the stem experiences pressure in the lateral direction. Particularly in the case of re-operation prostheses wherein stems are relatively long and extend deep into a femur, it has been found that the relatively thin walls, which are the same all the way round, are too resilient in the distal zone relative to the lateral loading. As a result, the proximal zone of the stem experiences excessive micromovements relative to the bone. However, since the relatively long re-operation stems extend into increasingly narrow portions of the femur, an increased resilience is desirable in the distal end zone. As a result, there are contra indications for the degree of resilience for the distal end of the stems.

Accordingly, it is an object to the invention to provide a stem for a prosthetic femoral head which is able to provide increased resilience at the distal end while being non-resilient relative to a lateral loading from a femoral head.

It is another object of the invention to improve the construction of the stem of a shank for a hip joint prosthesis for use in a re-operation prosthesis.

It is another object of the invention to provide a stem for a re-operation prosthesis which has resilience at the distal end along with rigidity in a proximal zone of the stem.

Briefly, the invention provides a stem for a prosthetic femoral head which has a distal zone of round cross-sectional shape disposed on a longitudinal axis, a hollow extending from a distal end of the zone toward a proximal zone of the stem on an increasing medial offset and with decreasing volume as well as a longitudinal slot communicating the hollow with a medial side of the stem.

The stem is constructed as part of the shank for a hip joint prosthesis which also includes a neck disposed on an axis which is angularly disposed relative to the longitudinal axis of the stem. In addition, the slot in the stem is disposed on an axis co-planar with the neck axis and the stem axis.

The effect of the increasing medial offset of the hollow from the distal zone in the proximal direction and the reduction in the volume of the hollow in the same direction is that the lateral wall thickness, particularly in the distal parts which are near the proximal zone, remains relatively substantial and, therefore, has substantial rigidity. Despite the rigidity in the top part of the distal zone of the stem, the required compressibility for the distal part of the stem is achieved adequately by the medially extending longitudinal slot and the medially extending hollow which is in communication with the slot.

One advantage of the construction of the stem is at the hollow may fill up with ingrowing tissue in the course of time with the tissue being nourished through the slot and kept viable Advantageously, the hollow and the slot extend at least substantially as far as the center of stem height, which is measured as the distance between the distal end of the stem and a proximal shoulder by way of which the lateral narrow side of the shank merges into a neck of the prosthesis.

In one embodiment, the hollow is in the form of a bore which extends angularly of the longitudinal axis of the stem. In another embodiment, the hollow is in the form of a series of stepped bores of decreasing diameter and increasing offset from the longitudinal axis of the stem. In this case, each bore is disposed on an axis parallel to the longitudinal axis of the stem.

These and other objects and advantages of the invention will become more apparent from the following detailed description taken in conjunction with the accompanying drawings wherein:

FIG. 1. illustrates a side view, partly in section, of a shank looking in a ventral/dorsal direction constructed in accordance with the invention for a re-operation prosthesis;

FIGS. 2a to 2f illustrate views taken on lines A—A to F—F of FIG. 1.;

FIG. 3. illustrates a modified shank constructed in accordance with the invention; and FIGS. 4a to 4f illustrate views taken on lines A—A to F—F of FIG. 3.

Referring to FIG. 1, the shank is constructed for a hip joint prosthesis, for example for a re-operation prosthesis. The shank includes a straight stem 1 which is disposed on longitudinal axis 3 and a neck 5 which is disposed on a neck axis 7 angularly of the longitudinal axis 3. In addition, a horizontal shoulder 4 is disposed in a transition zone between the stem 1 and neck 5 while a conical pin or peg 6 is disposed on the neck 5 in order to receive a joint head (not shown)

The stem 1 has a straight distal part which is of circular cross section (see FIGS. 2b to 2f) and a proximal part which is of elliptical or oval cross-section (see FIG. 2a). A lateral narrow side 2 of the proximal part is initially inclined at a slant to the longitudinal axis 3 and merges into the horizontal shoulder 4. On the medial side, the stem 1 merges into a curved transition which extends steplessly from the straight distal part into the prosthesis neck 5.

The stem 1 is formed in the cylindrical distal zone or part with a hollow 9 which extends from the distal end with an increasing medial offset and with a decreasing size towards the proximal end of the stem 1. As illustrated, the hollow 9 is in the form of a series of stepped bores 10c–10f (see FIGS. 2c to 2f) each of which is of decreasing diameter and increasing offset from the axis 3 of the stem 1 from the distal end of the stem toward the proximal end of the stem. As indicated in FIG. 1, each bore is disposed on an axis parallel to the longitudinal axis.

Further, the stem 1 is provided with a longitudinal slot 11 which communicates with the stepped bores 10c–10f of the hollow 9. As illustrated, the slot 11 is formed on the medial side and is disposed on an axis co-planar with a plane 8 formed by the neck axis 7 and the stem axis 3. Consequently, the hollow 9, on either side of the slot 11, is bounded by thin walled deformable flaps whose deformability increases distally with increasing volume of the hollow 9.

Referring to FIGS. 3 and 4, wherein like reference characters indicate like parts as above, the hollow 9 in the stem 1 may be in the form of a constant diameter bore which extends angularly of the longitudinal stem axis 3, that is, extends from the medial direction towards the lateral direction within the distal zone of the stem 1. As above, the longitudinal axis of the bore is disposed in the plane defined by the stem axis 3 and neck axis 7.

In the embodiment of FIGS. 3 and 4, the distally increasing resilience of the stem 1 is the result mainly of an increasing decrease in the lateral wall thickness as can be determined from FIGS. 4c to 4f.

The invention thus provides a stem for a prosthetic femoral head which can be readily used for a re-operation prosthesis. In this regard, the invention provides a stem which has an appropriate resilience at the distal while also a sufficient rigidity to the bending load applied by way of a femoral head to the stem.

What is claimed is:

1. A stem for a prosthetic femoral head comprising
    a distal zone of round cross-sectional shape disposed on a longitudinal axis;
    a series of stepped bores extending from a distal end of said zones towards a proximal zone of the stem, each bore having a diameter of decreasing size towards said proximal zone and an axle increasingly offset from and parallel to said longitudinal axis; and
    a longitudinal slot communicating said bores with a medial side of the stem.

2. A stem as set forth in claim 1 wherein said bores extend at least as far as the center of stem height as measured from said distal end to a shoulder thereof.

3. A shank for a hip joint prosthesis comprising
    a neck disposed on a first axis; and
    a stem disposed on a longitudinal axis angularly of said first axis, said stem including a series of stepped bores extending from a distal end of said stem with an increasing medial offset towards a proximal end of said stem, said bores being of decreasing diameter and being increasingly offset from said longitudinal axis from said distal end towards said proximal end of said stem, and a longitudinal slot communicating said bores with a medial side of said stem.

4. A shank as set forth in claim 3 wherein said slot is disposed on an axis co-planar with said first axis and said longitudinal axis.

5. A shank as set forth in claim 3 wherein each bore is disposed on an axis parallel to said longitudinal axis.

6. A shank as set forth in claim 3 wherein said stem has a circular cross-section.

* * * * *

UNITED STATES PATENT AND TRADEMARK OFFICE
CERTIFICATE OF CORRECTION

PATENT NO. : 4,921,501

DATED : May 1, 1990

INVENTOR(S) : ROBERTO GIACOMETTI

It is certified that error appears in the above-identified patent and that said Letters Patent is hereby corrected as shown below:

```
Column 2, line 9  "at" should be -that-
Column 3, line 25 "distal" should be -distal end-
Column 4, line 4  "axle" should be -axis-
```

Signed and Sealed this

Twenty-fifth Day of June, 1991

Attest:

HARRY F. MANBECK, JR.

Attesting Officer

Commissioner of Patents and Trademarks